United States Patent [19]
Theriault et al.

[11] Patent Number: 6,147,754
[45] Date of Patent: Nov. 14, 2000

[54] LASER INDUCED BREAKDOWN SPECTROSCOPY SOIL CONTAMINATION PROBE

[75] Inventors: Gregory A. Theriault, Encinitas; Stephen H. Lieberman, La Mesa; David S. Knowles; Leonard J. Martini, both of San Diego, all of Calif.

[73] Assignee: The United States of America as represented by the Secretary of the Navy, Washington, D.C.

[21] Appl. No.: 08/820,662

[22] Filed: Mar. 17, 1997

Related U.S. Application Data

[63] Continuation-in-part of application No. 08/630,653, Apr. 10, 1996, abandoned, and a continuation-in-part of application No. 08/401,601, Mar. 9, 1995, Pat. No. 5,757,484.

[51] Int. Cl.$^7$ ............................. G01J 3/443; G01N 21/63
[52] U.S. Cl. ................................................................ 356/318
[58] Field of Search ...................... 356/317, 318

[56] References Cited

U.S. PATENT DOCUMENTS

| | | |
|---|---|---|
| 5,128,882 | 7/1992 | Cooper et al. . |
| 5,316,950 | 5/1994 | Apitz et al. . |
| 5,379,103 | 1/1995 | Zigler . |

OTHER PUBLICATIONS

"Remote in–situ detection of heavy metal contamination in soils using a Fiber Optic Laser Induced Breakdown Spectroscopy (FOLIBS) System", Symposium Proceedings, Jun. 19–23, 1995.

*Primary Examiner*—F. L. Evans
*Attorney, Agent, or Firm*—Harvey Fendelman; Michael A. Kagan; Eric James Whitesell

[57] ABSTRACT

A LIBS cone penetrometer comprises a decoupling mirror to separate an excitation signal and a response signal, an optical fiber arranged with the decoupling mirror for receiving the excitation signal from an energy source and transmitting the response signal from a sample surface, and a cone penetrometer probe connected to the distal end of the optical fiber. The probe further comprises a collimating lens arranged with the optical fiber for collimating the excitation signal and for directing the response signal into the optical fiber. An internally reflecting prism is aligned with the collimating lens to deflect the excitation signal and the response signal between the collimating lens and the sample surface through a window in the side of the probe. A focusing lens is aligned with the prism and the window to reduce the spot size of the excitation signal and to collimate the response signal. The window is arranged with the focusing lens to maintain the distance between the focusing lens and the sample surface and to prevent outside matter from entering the probe.

13 Claims, 2 Drawing Sheets

LASER INDUCED BREAKDOWN SPECTROSCOPY SOIL CONTAMINATION PROBE

CROSS-REFERENCE TO RELATED APPLICATIONS

This application is a continuation-in-part under 37 CFR 1.53 of patent applications Ser. No. 08/630,653 filed Apr. 10, 1996 titled IN SITU MICROSCOPE IMAGING SYSTEM FOR EXAMINING SUBSURFACE ENVIRONMENTS, now abandoned, and a continuation-in-part of Ser. No. 08/401,601 filed Mar. 9, 1995 titled STANDOFF LASER INDUCED-BREAKDOWN SPECTROSCOPY PENETROMETER SYSTEM, now U.S. Pat. No. 5,757,484 both incorporated herein by reference thereto.

LICENSING INFORMATION

The invention described below is assigned to the United States Government and is available for licensing commercially. Technical and licensing inquiries may be directed to Harvey Fendelman, Legal Counsel For Patents, NCCOSC RDTE DIV CODE 0012, 53510 Silvergate Avenue Room 103, San Diego, Calif. 92152-5765; telephone no. (619)553-3818; fax no. (619)553-3821.

BACKGROUND OF THE INVENTION

The present invention relates to the identification of soil contaminants in subsurface environments. More specifically, but without limitation thereto, the present invention relates to a probe for laser induced breakdown spectroscopy of subsurface soil.

Increasing concern with soil and groundwater contamination and governmentally mandated requirements to clean up hazardous waste sites have created a need for cost effective systems and methods for determining the characterization of subsurface environments. In response to such needs, soil penetrating probes have been developed generally comprising a tube with a tapered tip which is forced into the ground. Instrumentation inside the tube detects various properties of the surrounding geological environment.

Laser Induced Breakdown Spectroscopy (LIBS) is a method for detecting the presence of various elements in a sample by directing a high power emission from a laser onto the sample to form a plasma. The plasma is then analyzed spectroscopically to determine the composition of the sample. The LIBS technique offers promise as a method suitable for use with a soil penetrating probe to detect heavy metal contamination in soil, because it is highly sensitive and requires no sample preparation. Usually the LIBS technique involves delivery of the laser energy to the sample through air due to the high power densities required to ionize the sample. Recently, fiber optic cable has been used successfully in LIBS measurements, allowing measurement of samples that are located at a considerable distance away from the excitation laser and analyzing equipment.

The use of cone penetrometry for elemental and molecular subsurface soil analysis using optical sensors has provided a lower cost alternative to traditional drilling and sampling methods and has been the subject of several recent patents.

U.S. Pat. No. 5,128,882 by Cooper et al. issued on Jul. 7, 1992 discloses a fiber optic cone penetrometer probe to irradiate the soil with UV or visible light to generate a fluorescence, reflection, or absorption spectrum of soil contaminants. The fluorescence spectroscopy described in this patent generates information for classifying certain molecular species, but does not form a plasma and is generally insensitive to atomic species, which are important to the identification of metal contamination.

U.S. Pat. No. 5,316,950 by Apitz et al. issued on May 31, 1994 discloses a method for interpreting fluorescence spectra from a cone penetrometer of the type described by Cooper using strain gauge data to compensate fluorescence measurements for variations in soil matrix.

U.S. Pat. No. 5,379,103 by Zigler issued on Jan. 3, 1995 discloses a dual mode probe using separate optical fibers to conduct excitation and response signals. In one mode the probe uses high peak power focused laser radiation to initiate a laser induced spark in a soil or groundwater sample. The optical emission from the sample is spectrum analyzed to identify and quantify elemental (atomic) species. In the other mode, relatively low peak power laser radiation is used to generate fluorescence to yield information from the irradiated sample about molecular species. Using separate optical fibers for the excitation and response signals becomes impractical as shorter focal lengths are used to increase the power density of the excitation signal, however, because the optical alignment of the fibers becomes more difficult. Another disadvantage is that the probe must be lowered down a well, requiring that a well be drilled first.

Although these recent developments represent considerable progress, much work remains to be done to solve problems such as delivering a high power pulse to a sample through an optical fiber without reducing the optical conductivity of the optical fiber, aligning and focusing the optics within the probe, and decoupling the excitation beam from the response signal. Therefore, there is a continued need for a cone penetrometer that can deliver a high power pulse of energy to a remotely located sample through an optical fiber and to decouple the response from the excitation pulse.

SUMMARY OF THE INVENTION

The LIBS cone penetrometer probe of the present invention is directed to overcoming the problems described above, and may provide further related advantages. No embodiment of the present invention described herein shall preclude other embodiments or advantages that may exist or become obvious to those skilled in the art.

A LIBS cone penetrometer of the present invention comprises a decoupling mirror to separate an excitation signal and a response signal, an optical fiber arranged with the decoupling mirror for receiving the excitation signal from an energy source and transmitting the response signal from a sample surface, and a cone penetrometer probe connected to the distal end of the optical fiber. The probe further comprises a collimating lens arranged with the optical fiber for collimating the excitation signal and for directing the response signal into the optical fiber. An internally reflecting prism is aligned with the collimating lens to deflect the excitation signal and the response signal between the collimating lens and the sample surface through a window in the side of the probe. A focusing lens is aligned with the prism and the window to reduce the spot size of the excitation signal and to collimate the response signal. The window is arranged with the focusing lens to maintain the distance between the focusing lens and the sample surface and to prevent outside matter from entering the probe.

An advantage of the LIBS cone penetrometer probe is that a high peak power spark pulse may be concentrated on a small area of a subsurface soil sample sufficient to ionize or form a plasma of elemental species present in soil and water.

Another advantage is that the emission spectra from the sample may be decoupled from the spark pulse without compromising the power level of the spark pulse or introducing wavelength dependence that could attenuate the response signal.

Still another advantage is that site mapping may be done in real time, obviating the expense of taking data to maximum depth for each penetration.

Yet another advantage of the real time site mapping afforded by the present invention is that decisions on which areas to map may be made in real time, with the result that fewer holes are bored into clean soil.

Another advantage is that the cone penetrometer technique of the present invention avoids lifting drilling material to the surface that would require special handling as hazardous waste.

Still another advantage of the LIBS cone penetrometer is that the internal components are protected from contamination by liquids, providing the capability to operate below the water table.

The features and advantages summarized above in addition to other aspects of the present invention will become more apparent from the description, presented in conjunction with the following drawings.

DESCRIPTION OF THE INVENTION

The following description is presented solely for the purpose of disclosing how the present invention may be made and used. The scope of the invention is defined by the claims.

Figure 1:
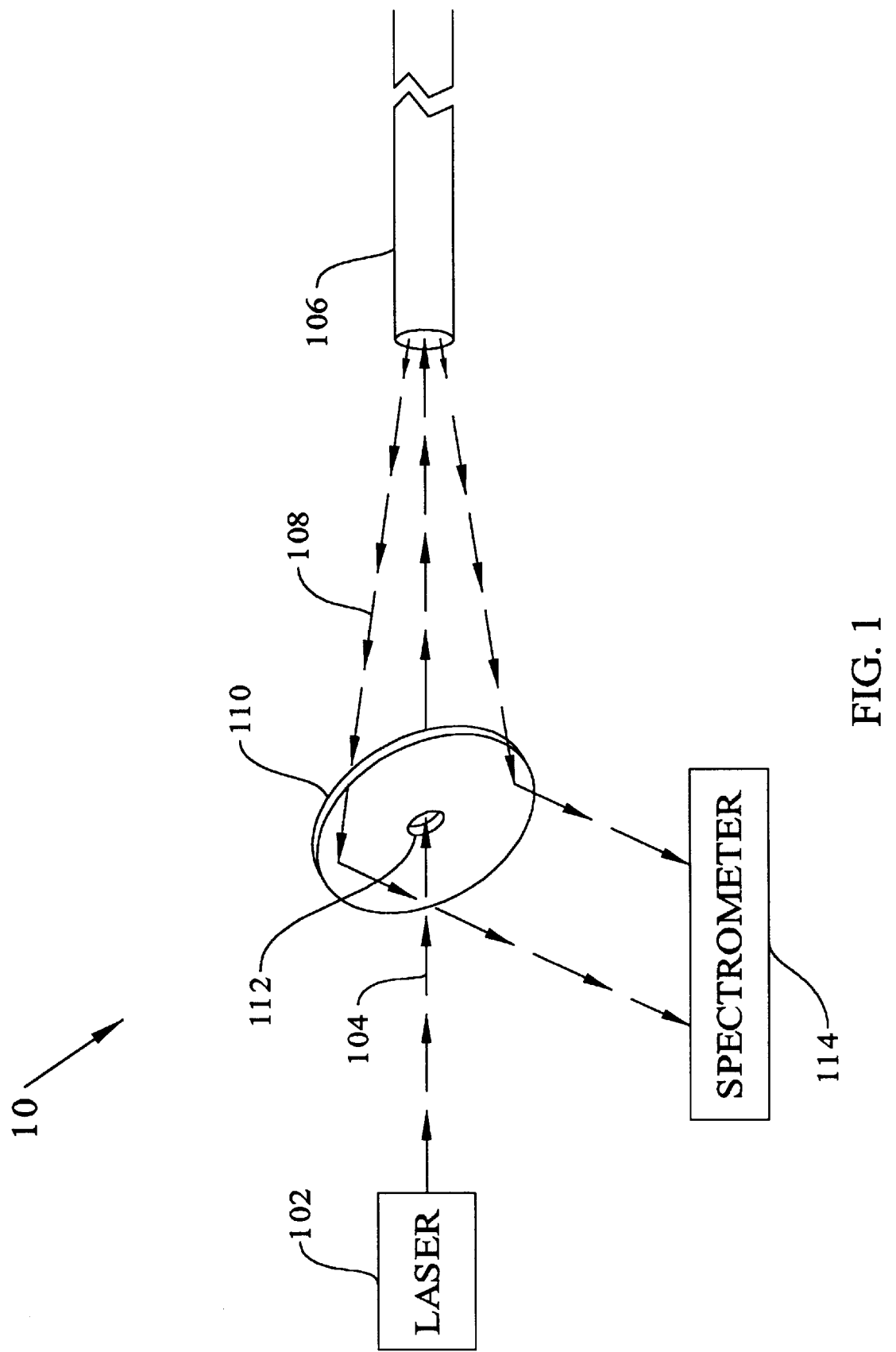
FIG. 1 is an illustration of a decoupling arrangement of the present invention.

FIG. 1 illustrates a decoupling arrangement 10 for decoupling an excitation signal 104 emitted by a laser source 102 and a response signal 108 exiting from an optical fiber 106. A decoupling mirror 110 has a beam aperture 112 through which excitation signal 104. passes to enter optical fiber 106. Decoupling mirror 110 may be, for example, a surface polished metallic mirror having a diameter of 2 in. and a center hole having a diameter of ⅛ in. drilled at an angle corresponding to the orientation of decoupling mirror 110 with excitation signal 104, typically 45 deg. A dielectric mirror may also be used in applications where wavelength dependence may be used to advantage. Response signal 108 exits optical fiber 106 within a beamwidth 108 and is deflected to a detector 114 by decoupling mirror 110 except for the fraction coincident with excitation signal 104 that escapes through aperture 112. In this way decoupling arrangement 10 transmits excitation signal 104 without interposing any materials that would reduce the ionization capability of excitation signal 104 and decouples response signal 108 without interposing wavelength sensitive materials that could alter the signal received by detector 114. Detector 114 is exemplified in FIG. 1 as a spectrometer.

Laser source 102 may be, for example, a Nd:YAG laser operating at 1064 nm. The Nd:YAG laser could also be operated at 532 nm by using appropriate doubling crystals to generate the second harmonic. Both the 1064 nm and 532 nm wavelengths are transmitted by commercially available fused silica core optical fibers with only slight attenuation at the power densities required to generate a laser induced spark.

The total energy output of a Nd:YAG Q-switched laser may be optimized for optical fiber transmission by delaying the Q-switch timing by several hundred microseconds from the time normally selected to generate maximum peak power from the laser. This is done to increase the output pulse width from the typical 5–8 ns to approximately 20 ns, distributing the energy at a lower peak power over a longer pulse width. Lowering the peak power increases the amount of energy in the excitation signal that may be conducted through the optical fiber without causing damage to the optical fiber that could degrade its transmission efficiency. Generally, the higher the pulse energy below the damage threshold of the optical fiber, the higher the sample ionization or spark temperature and resulting response signal. The typical pulse width of the response signal is several hundred nanoseconds, which suggests that a burst of several 20 ns pulses may be used to increase the spark temperature.

Figure 2:
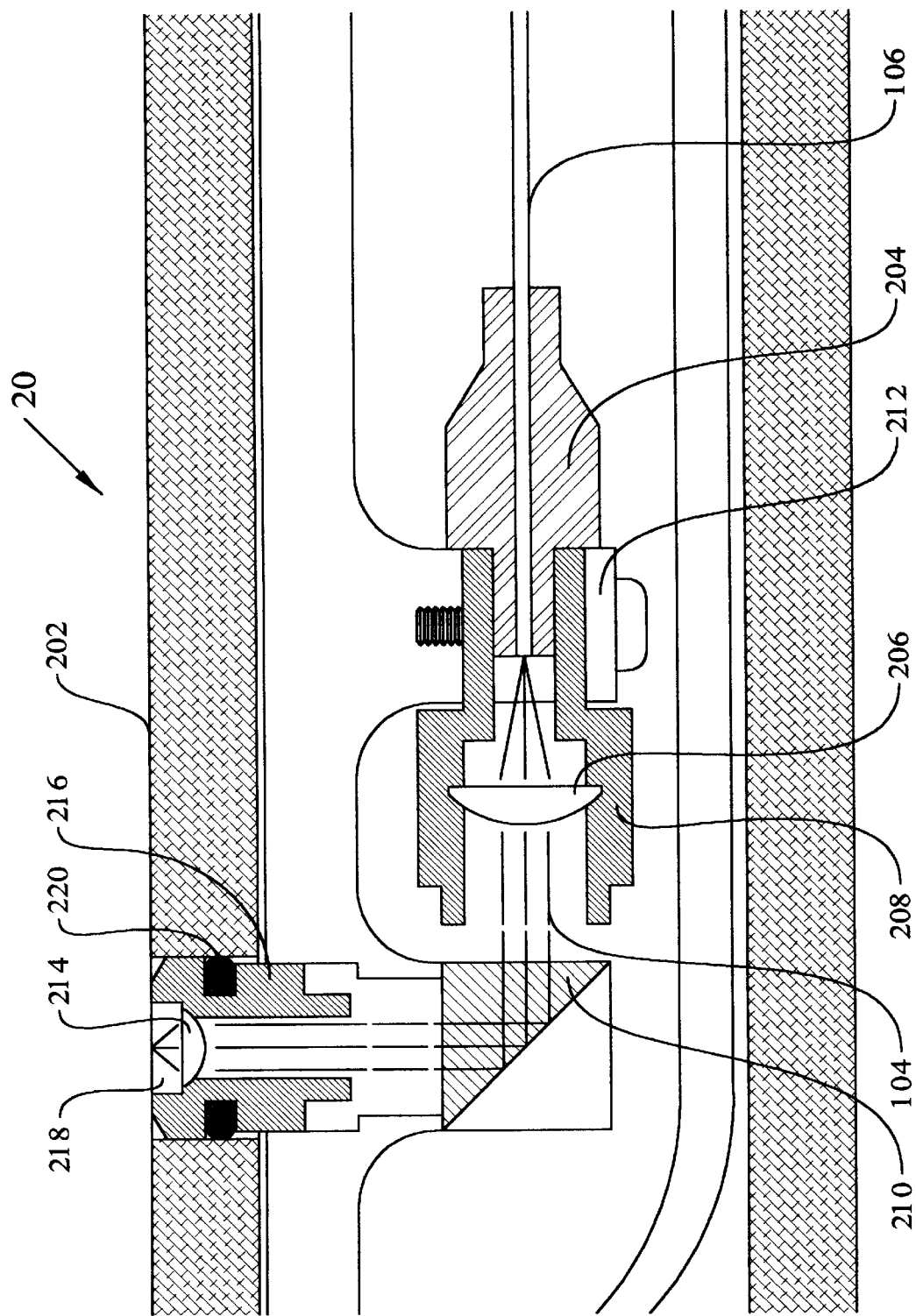
FIG. 2 is a cross section of a cone penetrometer probe of the present invention.

Referring now to FIG. 2, excitation signal 104 is conducted by optical fiber 106 into probe 202 to a terminator 204 held by optical mounting 208. A clamp 212 secures terminator 204 inside probe 202 to maintain optical alignment during mechanical stresses encountered while deploying probe 202. A collimating lens 206 mounted in a lens holder 208 collimates excitation signal 104 exiting from optical fiber 106. A prism 210 mounted inside probe 202 deflects excitation signal 104 toward window 218 on the side of probe 202. Prism 210 uses internal reflection rather than a reflective coating that would be wavelength dependent and also subject to damage from excitation signal 104. A focusing lens 214 mounted at window 218 by a sealed mounting 216 concentrates excitation signal 104 outside probe 202 to provide high power density for ionization of the sample surface (not shown). Window 218 is substantially transparent to excitation signal 104 and response signal 108, and maintains the distance between focusing lens 214 and the sample surface outside probe 202 at the focal length of focusing lens 214. By way of example, window 218 may be made of sapphire or diamond. Sealed mounting 216 facilitates the replacement of window 218 and prevents soil and water from entering probe 202 by, for example, an O-ring 220.

Focusing lens 214 may be positioned by focusing a microscope mounted on a vertical axis translation stage onto the surface of window 218. With laser source 102 set at a sufficiently low power level for safety and focusing lens 214 placed against window 218, the microscope is refocused on the minimum spot size produced by excitation signal 104. The amount of translation required to refocus the microscope is the distance needed to move the focusing lens to position the spot image at the exterior surface of window 218. A shim may be used to separate focusing lens 214 from window 218 inside a threaded lens holder similar to that used to align collimating lens 206.

Optical mounting 208 provides strain relief for optical fiber 106 and houses the optical configuration that collimates and deflects excitation signal 104 and response signal 108. Terminator 204 may be, for example, an SMA connector threaded into optical mounting 208. Optical mounting 208 holds collimating lens 206 at its focal length from optical fiber 106. By way of example, collimating lens 206 may have a focal length of 10 mm and focusing lens 214 may have a focal length of 4 mm. The ratio of the focal lengths determines the spot diameter in this arrangement. For example, a 600 micron core diameter fiber re-images to a 600 micron $\times(4/10)=240$ micron spot diameter at the sample surface. Because the spark initiation threshold and the fiber damage threshold are fairly close together, approximately 0.3 GW/cm² and 1 GW/cm² respectively, focusing is an effective method of achieving the desired spot intensity on the sample surface without approaching the damage threshold of optical fiber 106.

In operation, excitation signal 104 enters optical fiber 106 as shown in FIG. 1 and exits optical fiber 106 inside probe 202 as shown in FIG. 2. The energy of excitation signal 104 ionizes the sample surface outside window 218 causing a spark. Energy from the spark comprising response signal 108 is collimated by focusing lens 214, is deflected by prism 210, and is focused onto optical fiber 106 by collimating lens 206. Response signal exits optical fiber 106 as shown in FIG. 1 and is reflected by decoupling mirror 110 to detector 114. Since the spark initiation threshold of soil is typically close to the damage threshold of optical fiber 106, reducing the spot size of excitation signal 104 to a size smaller than the fiber core diameter increases the power density (power per unit area) at the sample surface well above the spark threshold. Because excitation signal 104 converges over the short focal length of focusing lens 214, small variations in the sample surface can result in large differences in the power density. These differences in power density may introduce inconsistency in successive measurements. The compression of the window 218 against the sample surface helps to ensure a that the sample surface is maintained at the focal length of focusing lens 214 to effect uniform power density. The small spot size also necessitates careful optical alignment to efficiently couple the response signal, a problem which the present invention solves by the inherently self-aligning properties of the single optical fiber arrangement.

Other modifications, variations, and applications of the present invention may be made in accordance with the above teachings other than as specifically described to practice the invention within the scope of the following claims.

We claim:

1. A cone penetrometer comprising:

a decoupling mirror having an aperture to pass an excitation signal and a reflective surface for deflecting a response signal emitted by a sample surface;

an optical fiber operably coupled to said decoupling mirror for conducting said excitation signal and said response signal;

a probe enclosure operably coupled to a distal end of said optical fiber;

a collimating lens operably coupled to said optical fiber and said probe enclosure for collimating said excitation signal exiting said optical fiber and for directing said response signal into said optical fiber;

an internally reflecting prism operably coupled to said collimating lens and said probe enclosure for deflecting said excitation signal and said response signal between said collimating lens and said sample surface;

a focusing lens operably coupled to said prism and said probe enclosure having a focal length for reducing spot size of said excitation signal and for collimating said response signal; and a substantially transparent window operably coupled to said focusing lens and said probe enclosure for maintaining a distance between said focusing lens and said sample surface substantially equal to said focal length of said focusing lens.

2. The cone penetrometer of claim 1 further comprising a source of said excitation signal.

3. The cone penetrometer of claim 1 wherein said excitation signal has a wavelength of approximately one of 1064 nm and 532 nm.

4. The cone penetrometer of claim 1 wherein said optical fiber comprises a single fused silica core.

5. The cone penetrometer of claim 1 wherein said decoupling mirror is one of a metallic mirror and a dielectric mirror.

6. The cone penetrometer of claim 1 wherein said decoupling mirror has a diameter of about 2 in. and a center hole about ⅛ in. in diameter formed at an angle corresponding to the orientation of said decoupling mirror with respect to said excitation signal.

7. The cone penetrometer of claim 1 further comprising a strain relief operably coupled to said probe enclosure and said optical fiber.

8. The cone penetrometer of claim 1 further comprising an optical mounting operably coupled to said probe enclosure and said collimating lens.

9. The cone penetrometer of claim 1 further comprising a sealed mounting operably coupled to said probe enclosure and said window to prevent outside matter from entering said probe enclosure.

10. The cone penetrometer of claim 1 wherein said focusing lens and said collimating lens have focal lengths selected to cause said excitation signal to have an intensity below a damage threshold inside said optical fiber and above a desired intensity at said sample surface.

11. The cone penetrometer of claim 1 wherein said window comprises at least one of sapphire and diamond.

12. A cone penetrometer comprising:

a decoupling mirror having an aperture to pass an excitation signal and a reflective surface for deflecting a response signal emitted by a sample surface;

an optical fiber operably coupled to said decoupling mirror for conducting said excitation signal and said response signal;

a probe enclosure operably coupled to a distal end of said optical fiber;

a collimating lens operably coupled to said optical fiber and said probe enclosure for collimating said excitation signal exiting said optical fiber and for directing said response signal into said optical fiber;

an internally reflecting prism operably coupled to said collimating lens and said probe enclosure for deflecting said excitation signal and said response signal between said collimating lens and said sample surface;

a focusing lens operably coupled to said prism and said probe enclosure having a focal length for reducing spot size of said excitation signal and for collimating said response signal;

a substantially transparent window operably coupled to said focusing lens and said probe enclosure for maintaining a distance between said focusing lens and said sample surface substantially equal to said focal length of said focusing lens;

an optical mounting operably coupled to said probe enclosure and said collimating lens;

a sealed mounting operably coupled to said probe enclosure and said window to prevent outside matter from entering said probe enclosure;

a strain relief operably coupled to said probe enclosure and said optical fiber; and a source of said excitation signal, wherein said excitation signal has a wavelength of approximately one of 1064 nm and 532 nm;

wherein said optical fiber comprises a single fused silica core;

wherein said decoupling mirror is one of a metallic mirror and a dielectric mirror;

wherein said decoupling mirror has a diameter of about 2 in. and a center hole about 1/8 in. in diameter formed at an angle corresponding to the orientation of said decoupling mirror with respect to said excitation signal;

wherein said focusing lens and said collimating lens have focal lengths selected to cause said excitation signal to have an intensity below a damage threshold inside said optical fiber and above a desired intensity at said sample surface; and wherein said window comprises at least one of sapphire and diamond.

13. A cone penetrometer comprising:

a decoupling mirror having an aperture to pass an excitation signal and a reflective surface for deflecting a response signal emitted by a sample surface;

an internally reflecting prism operably coupled to said decoupling mirror for deflecting said excitation signal and said response signal between said decoupling mirror and said sample surface;

a focusing lens operably coupled to said prism having a focal length for reducing spot size of said excitation signal and for collimating said response signal;

and a substantially transparent window operably coupled to said focusing lens for maintaining a distance between said focusing lens and said sample surface substantially equal to said focal length of said focusing lens.

* * * * *